US008478410B2

(12) United States Patent
Kivlighan (10) Patent No.: US 8,478,410 B2
(45) Date of Patent: Jul. 2, 2013

(54) ELECTRONIC NEURAL RESONATOR

(75) Inventor: Michael F. Kivlighan, Waynesboro, VA (US)

(73) Assignee: Michael F. Kivlighan, Waynesboro, VA (US)

( * ) Notice: Subject to any disclaimer, the term of this patent is extended or adjusted under 35 U.S.C. 154(b) by 648 days.

(21) Appl. No.: 12/585,179

(22) Filed: Sep. 8, 2009

(65) Prior Publication Data

US 2010/0222850 A1    Sep. 2, 2010

Related U.S. Application Data

(63) Continuation-in-part of application No. 11/349,967, filed on Feb. 9, 2006, now Pat. No. 7,587,245.

(60) Provisional application No. 60/651,065, filed on Feb. 9, 2005, provisional application No. 60/671,103, filed on Apr. 14, 2005.

(51) Int. Cl.
*A61N 1/18* (2006.01)

(52) U.S. Cl.
USPC .............................. 607/39; 607/100; 607/59

(58) Field of Classification Search
USPC .......................................................... 607/48
See application file for complete search history.

(56) References Cited

U.S. PATENT DOCUMENTS

| | | | | |
|---|---|---|---|---|
| 5,983,141 | A * | 11/1999 | Sluijter et al. | 607/100 |
| 6,520,903 | B1 * | 2/2003 | Yamashiro | 600/9 |
| 2004/0181261 | A1 * | 9/2004 | Manne | 607/39 |

* cited by examiner

*Primary Examiner* — Carl H Layno
*Assistant Examiner* — Jon Eric C Morales
(74) *Attorney, Agent, or Firm* — Dale R. Jensen (57) ABSTRACT

A procedure electrically stimulates a nerve or group of nerves. Unlike conventional systems this procedure is tuned to target a large or small group of neurons using noninvasive electromagnetic induction. This system is capable of doing this by using the principles of the alternating current in a capacitance inductance series resonance circuit. In this system the nerve resonator treats the neuron like a thin conductor placed between the plates of a capacitor in series with an inductor and then tuned to resonate with the appropriate frequency of alternating current. The system could also be inductance tuned for a given frequency. Once the system is tuned, the current amplitude in the entire circuit including the thin conductor or nerve fiber can be externally controlled.

26 Claims, 9 Drawing Sheets

ELECTRONIC NEURAL RESONATOR

CROSS-REFERENCE TO RELATED APPLICATION(S)

This application is a continuation-in-part and claims the benefit of U.S. patent application Ser. No. 11/349,967, filed Feb. 9, 2006, now U.S. Pat. No. 7,587,245, U.S. provisional patent application Ser. No. 60/651,065, filed Feb. 9, 2005 and U.S. provisional patent application Ser. No. 60/671,103, filed Apr. 14, 2005.

BACKGROUND OF THE INVENTION

Figure 1:
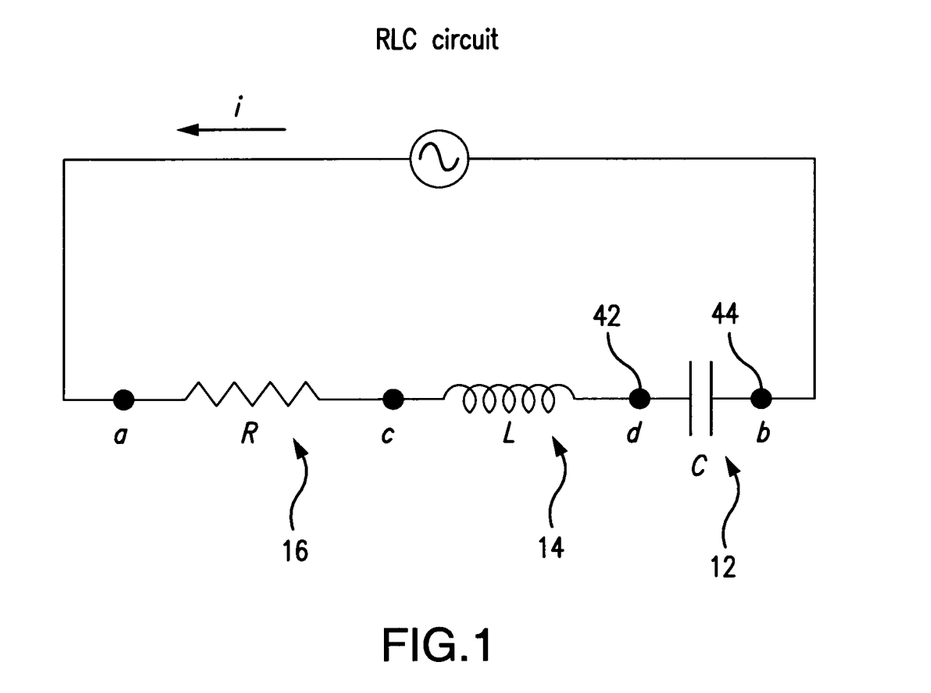
FIG. 1 depicts a conventional RLC circuit.

If the plates of a capacitor are separated and a thin conductor is placed between the plates and does not touch either plate the overall capacitance is equal to the capacitance created by the distance between each plate and the thin conductor. As seen in FIG. 1, if a capacitor 12 is placed in series with an inductor 14 and a resistor 16 and the circuit is caused to resonance with an alternating current the current is the same in all parts of the circuit. A thin conductor placed between the separated plates of the capacitor in an RLC circuit acts just like a conductor in the circuit separated by two separate capacitors in an RLC circuit. Since the thin conductor acts like another conductor in the circuit separated by two separate capacitors, it is now part of a new RLC circuit and a current will be induced on it as if it was just another conductor in the resonating circuit.

Figure 2:
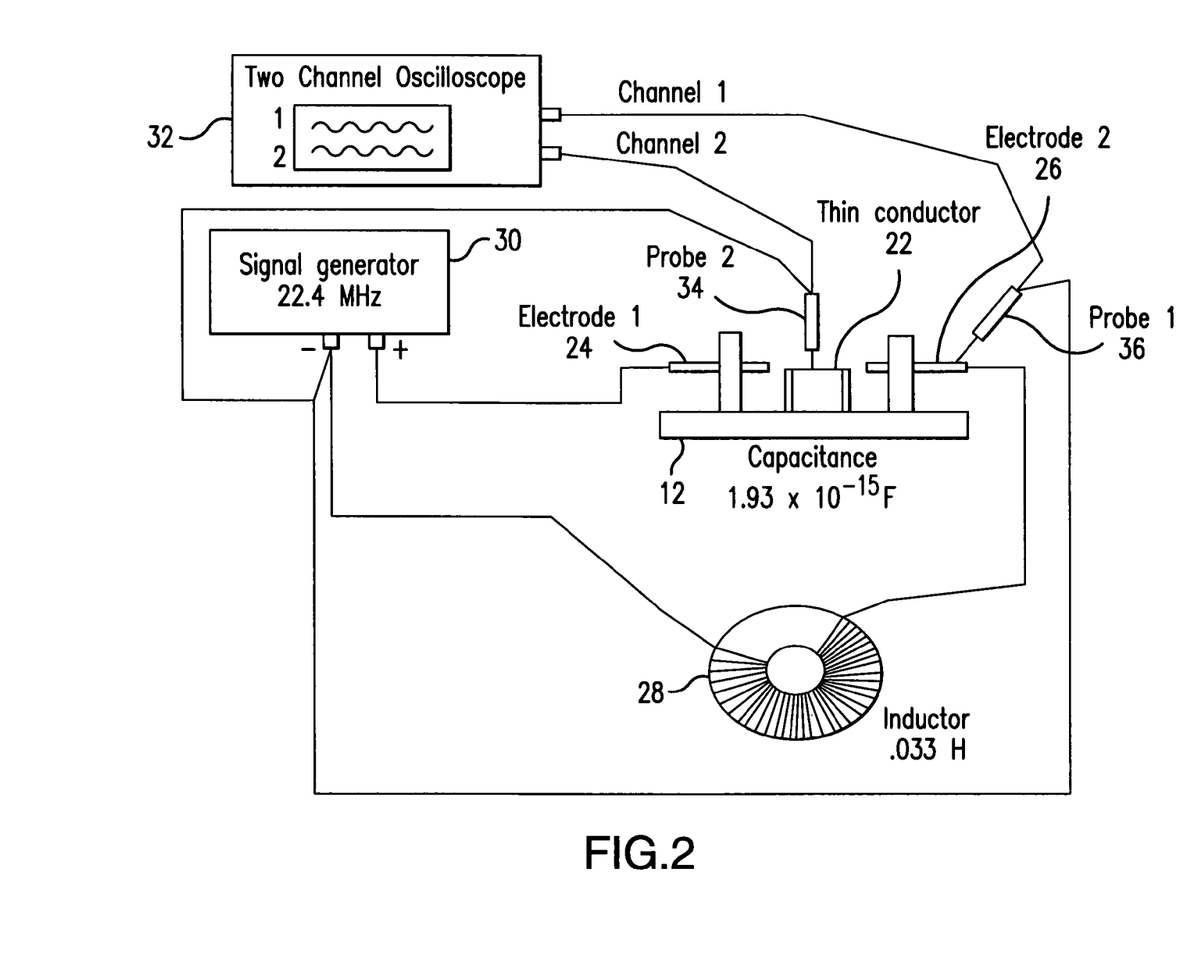
FIG. 2 depicts an RLC circuit having an alternative capacitor.

When the reactance of the inductor is equal to the reactance of the capacitors in the circuit the circuit will resonate at a natural frequency and there is only resistance in the circuit. This resistance can be varied externally. Since all the current is uniform in a resonating circuit the externally varied current will vary the current induced in the thin conductor between the plates of the capacitor because the thin conductor is now part of the circuit. This concept can be demonstrated experimentally by placing a fine wire 22, separated by air space, between two conductors 24,26 as shown in FIG. 2. The conductors are then placed in series with an inductor 28 and caused to resonate using a signal generator 30 connected in series. It can then be shown using an oscilloscope 32 that at resonance the current in the isolated thin wire is the same as any other point in the circuit and its amplitude can be controlled externally by varying the signal generator current output.

SUMMARY OF THE INVENTION

A procedure electrically stimulates a nerve or group of nerves. Unlike conventional systems this procedure is tuned to target a large or small group of neurons using noninvasive electromagnetic induction. This system is capable of doing this by using the principles of the alternating current in a capacitance inductance series resonance circuit. In this system the nerve resonator treats the neuron like a thin conductor placed between the plates of a capacitor in series with an inductor and then tuned to resonate with the appropriate frequency of alternating current. The system could also be inductance tuned for a given frequency. Once the system is tuned, the current amplitude in the entire circuit including the thin conductor or nerve fiber can be externally controlled.

This electrical medical device is based on three physical phenomena. Examining the equations for a series resonate RLC circuit illustrates the first. For a given resonate natural frequency ($\omega_0$) there is a unique inductor (L) for a given capacitance (C). This relationship is shown in the equation for a resonating RLC circuit.

$$\omega_0^2 = \frac{1}{LC}.$$

The second physical phenomenon is that alternating currents with frequencies of the order of $10^6$ Hz do not interfere appreciably with nerve processes and can be used for therapeutic heating. The nerve axon is conductive due to fact that it contains an electrolyte and once it is exposed to changing electromagnetic field it experiences electrolysis.

The third physical phenomenon is that a dielectric material between the plates, of the parallel plate capacitor, decreases the potential. This phenomenon is because a charge builds up on the surface of the dielectric. Some of the field lines pass through the dielectric material and some do not. The field lines that do not pass through the dielectric are responsible for the voltage decrease and the dielectric surface charge.

This disturbance can cause displacement currents in the dielectric material. These displacement currents would affect a conductive fiber in the dielectric. This conductive fiber represents the target nerve axon and the dielectric represents the surrounding tissue. Since the charge Q dose not change and the voltage ($V_0$) is greater than (V) the capacitance is increased by the dielectric. Since the tissue act like a dielectric it only increases the capacitance between the electrode and target nerve. The following equation, for a capacitor with constant charge Q, shows that a decrease in voltage results in an increase in capacitance.

$$C = \frac{Q}{V}$$

The applications for neutral resonating are numerous. For example, using the applied resonating electric field to target and incinerate the infected neuron could cure genital herpes. The applied current will cause electrolysis on the electrolyte conductor. Placing one electrode over the appropriate ganglion and the other electrode on the lesion targets the infected neuron. The ganglion contains the nucleus of the neurons for a certain sensory system. Therefore a disk shaped electrode is placed over the ganglia on the back. The lesion indicates the point on the skin where the infected nerve is closest. A point electrode is placed over it. The system can also be used for pain relief anywhere on the body. The area treated could be large or small according to the size of the electrodes. It could be used to treat other infections of the nervous system. Unlike other systems the neuron can be targeted and the current in the neuron can be tuned and externally adjusted. This system can also indicate the conductivity of the neuron because as its changes the system capacitance will change, changing the natural frequency of the system.

DETAILED DESCRIPTION OF THE INVENTION

Referring back to FIG. 2, the thin wire 22 acts as the thin conductor and two cylinder conductors 24,26 represent the plates of the capacitor. These cylinders are separated and held in space in a wood fixture. The thin wire is placed between the cylinders. This fixture is a replication of the capacitance model. The conductive cylinders are the original capacitors plates and the thin wire is the thin conductor between the plates of the original capacitor. The thin conductor acts like the target nerve because the nerve is conductive. The capacitance was calculated using the area of the end of each cylinder and the distance between them. For this model the capacitance was calculated to be $1.93 \times 10^{-15}$ F. This capacitance was calculated from the following formula.

$$C = \epsilon_0 \frac{A}{d}$$

Since the system will be eventually tuned only an approximation of the capacitance is necessary to establish an appropriate inductance. Therefore the affect of the air and wire can be excluded from the equation.

Once the capacitance is known an inductance can be calculated for a natural frequency. A frequency of 20 MHz is above the range of nervous system perception. So for this experiment an inductance of 0.033 H will be needed to make this circuit, containing a capacitance of $1.93 \times 10^{-15}$ F, resonate at a natural frequency of 20 MHz. This can be shown by using the equations for an RLC series resonate circuit and solving for inductance for a given natural frequency and capacitance.

$$f_r = \frac{1}{2\pi\sqrt{LC}}$$

In the experiment the capacitance model was connected in series with the inductor 28 and a variable RF signal generator 30, as seen in FIG. 2. The circuit was tuned to resonate by adjusting the frequency on the signal generator. The signal was monitored using an oscilloscope 32 with two probes 34,36 connected on the circuit. At approximately 20 MHz the circuit starts to resonate and both probes start to have the same reading. This is consistent with the fact that the current is equal across the circuit of a resonating RLC circuit. Once resonance is achieved, by tuning the frequency, the amplitude of the current, anywhere on the circuit, obeys Ohms law and can be controlled by varying the resistance anywhere in the circuit.

V=IR

This is consistent with the equations for a resonating RLC series circuit. Placing the oscilloscope probe anywhere on the experimental circuit at resonance, and obtaining the same results, experimentally verifies this equation. These results prove that a thin conductor, representing a conductive nerve isolated in space, can be targeted with two electrodes and tuned to resonate. At resonance the thin conductor essentially becomes part of the circuit and its current amplitude can be adjusted externally. This targeted current can be used to directly electrically stimulate the nerve.

If the circuit is resonating the equations for can be defined by the following equations for a resonating RLC circuit.

Series Resonance $X_L = X_C$ $\omega_0 L = \frac{1}{\omega_0 C}$ $\omega_0^2 = \frac{1}{LC}$ $Z = R$ $V_L = V_C$ $V_L = IX_L$ $V_C = IX_C$ $V_R = IR$ V = Voltage (V)(volts)

I = Current (A)(amps)

R = Resistance $(V \cdot A^{-1})(\Omega)$(ohm)

L = Inductance $(H)(V \cdot s \cdot A^{-1})$

C = Capacitance (F)

f = Frequency (Hz)(cycles/sec.)

$\omega$ = Angular− frequency (rad./sec.)

$\omega_0$ = Natural − frequency (rad./sec.)

X = Reactance $(V \cdot A^{-1})(\Omega)$(ohm)

Z = Impedance $(V \cdot A^{-1})(\Omega)$(ohm)

The following equations are for resistance, capacitance and inductance.

Resistance $R = \frac{\rho l}{A}$

V = IR

Capacitance $C = \frac{Q}{V_{ab}}$ $C = \frac{\varepsilon A}{d}$ $i = C \frac{dv}{dt}$ Inductance $L = \mu_0 \frac{N^2 A}{l}$ $v = L \frac{di}{dt}$ $\rho$ = Resistivity $(\Omega \cdot m)$ A = Area $(m^2)$ l = Length (m)

$\varepsilon_0$ = Premittivity $(8.854 \times 10^{12} C^2 \cdot N^{-1} \cdot m^{-2})$ $\mu_0$ = Permeability $(4\pi \times 10^{-7} Wb \cdot A^{-1} \cdot m^{-1})$ K = Dielectric − constant -continued Q = Charge (C)(coulmb)

N = Number − turns

Figure 3:
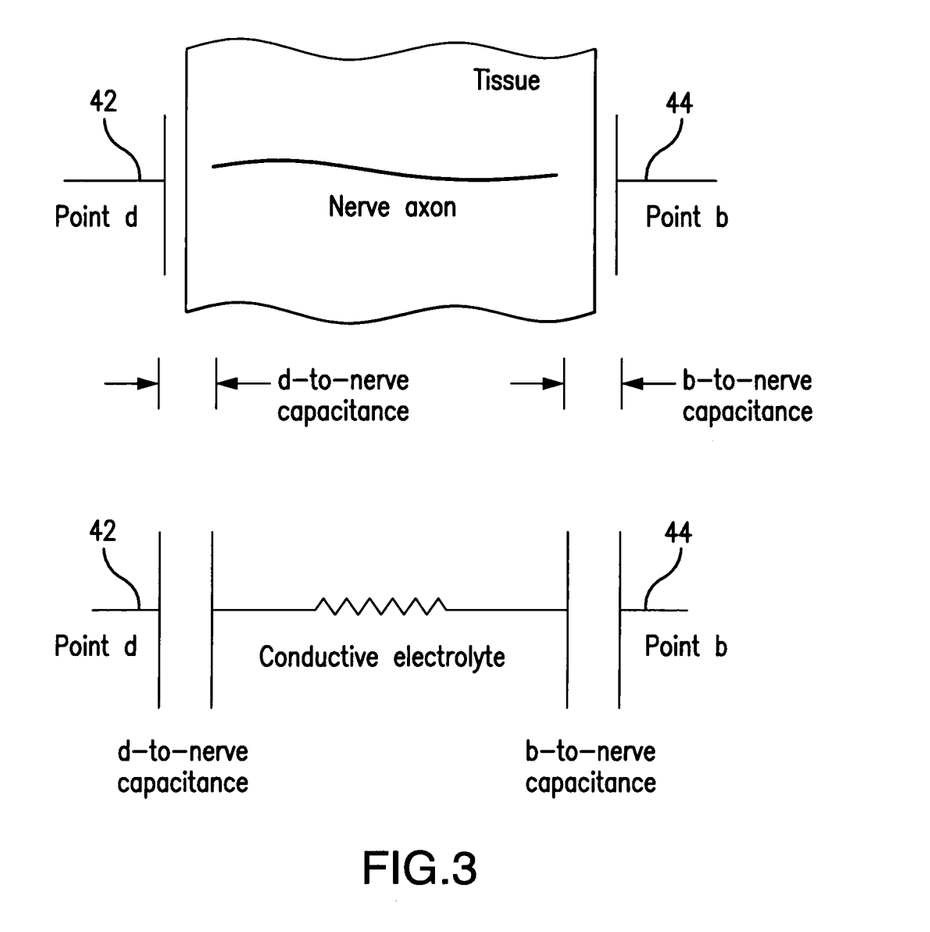
FIG. 3 depicts a capacitance model using a nerve.

If the two plates of the original capacitor in the RLC circuit 10 are replaced with electrodes 42,44 and if the two electrodes are placed correctly along a target nerve 45, the nerve acts like the thin conductor 22 placed between the separated plates of the original capacitor. The comparison is depicted in FIG. 3. This total capacitance can then be placed in series with the proper inductance and caused to resonate at their natural frequency with an alternating current. The nerve 45 will then act like the thin conductor connecting two capacitors in series in the RLC circuit. For a given natural frequency this capacitance will act like one total capacitance and can be caused to resonate if connected in series with the proper inductance.

Resonance is achieved in this constant capacitance series circuit by tuning the inductance or by tuning the frequency. Because the nerve fiber is conductive it becomes part of the circuit separated by two capacitors in series just like the thin conductor placed between the separated plates of the capacitor in the RLC circuit. Once resonance is achieved we can externally control the current in the nerve by controlling an external resistance for a given voltage. This is because at resonance the AC current in the RLC circuit obeys ohms law as if it was a DC circuit.

V=IR

It does not matter if there is tissue separating the electrodes from the nerve. The ends of the electrodes themselves are electrically insulated. This is because a capacitor with a dialectic placed between its plates still has capacitance. The capacitance of a capacitor is found to increase with the presents of a dielectric between its plates and the tissue acts as a dielectric.

The nerve resonator is tuned to optimize the current on the target nerve similar to the way a radio is tuned to receive a given signal. This system views the nerve as conductor separated by two capacitors in a circuit. A current in the nerve can then be resonated at a certain frequency using the proper inductance. This is similar to inductance tuning a radio receiver for a given capacitance and a certain frequency.

Resonance can be achieved by vibrating a system at its natural frequency. The most common example of mechanical resonance is when a wine glass is shattered with sound waves. If a wine glass is vibrated at its natural frequency even sound waves of relatively low amplitude can cause the glass to shatter. It could be possible to destroy the axon of a nerve cell with the same phenomenon because a system can be electrically resonated. The nerve axon could be destroyed using an alternating current. If the system is oscillated with an alternating current at its natural frequency the nerve axon could be destroyed much the same way as the wine glass.

Figure 4:
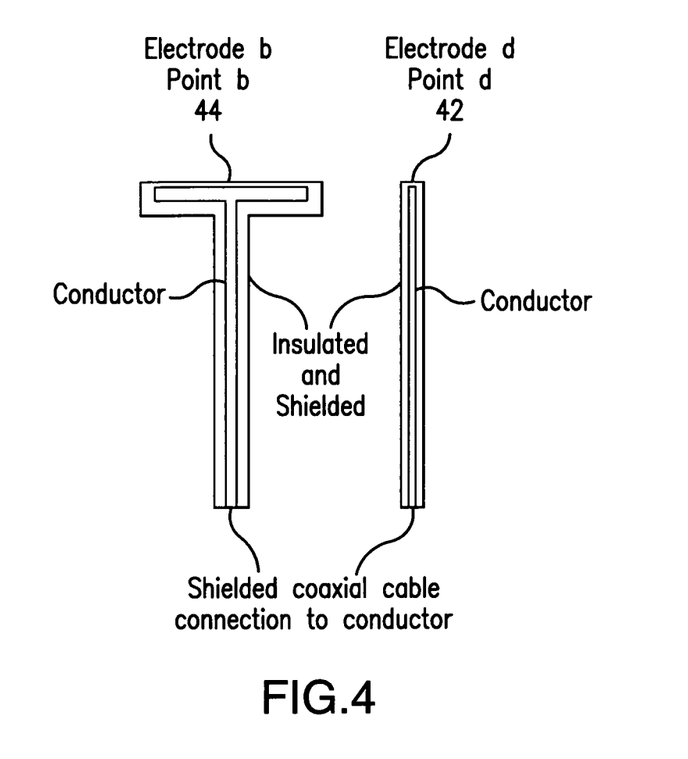
FIG. 4 depicts electrodes used with the invention.

Insulated and shielded conductors can be used as electrodes 42, 44, depicted in FIG. 4. If the electrodes are placed at opposite sides of the target axon an alternating current could be induced on that axon by varying the frequency or inductance. Tuning the frequency or inductance in the circuit will accommodate the new capacitance created between the electrodes with the target axon between them. The electrolyte in the neuron is conductive. As the current is increased in the electrolyte it will experience electrolysis. The electrolysis will cause the electrolyte to become a dielectric due to thermal breakdown.

The neural resonator can be used to target infected neurons. One example of a neural infection is the herpes virus. The herpes virus penetrates the skin, at the site of a lesion, and enters the nervous system through the sensory nerve endings. Then it follows the nerve axon to a single nerve cell nucleus located in the ganglion. Once the virus reaches the nerve cell nucleus it multiplies. The viral offspring then follow the same nerve axon back to the skin surface. They show up as a lesion. The nerve axon is electrically conductive. Therefore it is a conductive path between the lesion and the infected nerve cell nucleus. In the case of genital herpes the lesion is located on the genitals. The infected nerve cell nucleus is located in the ganglion at the base of the spine, seen in FIG. 5.

Figure 5:
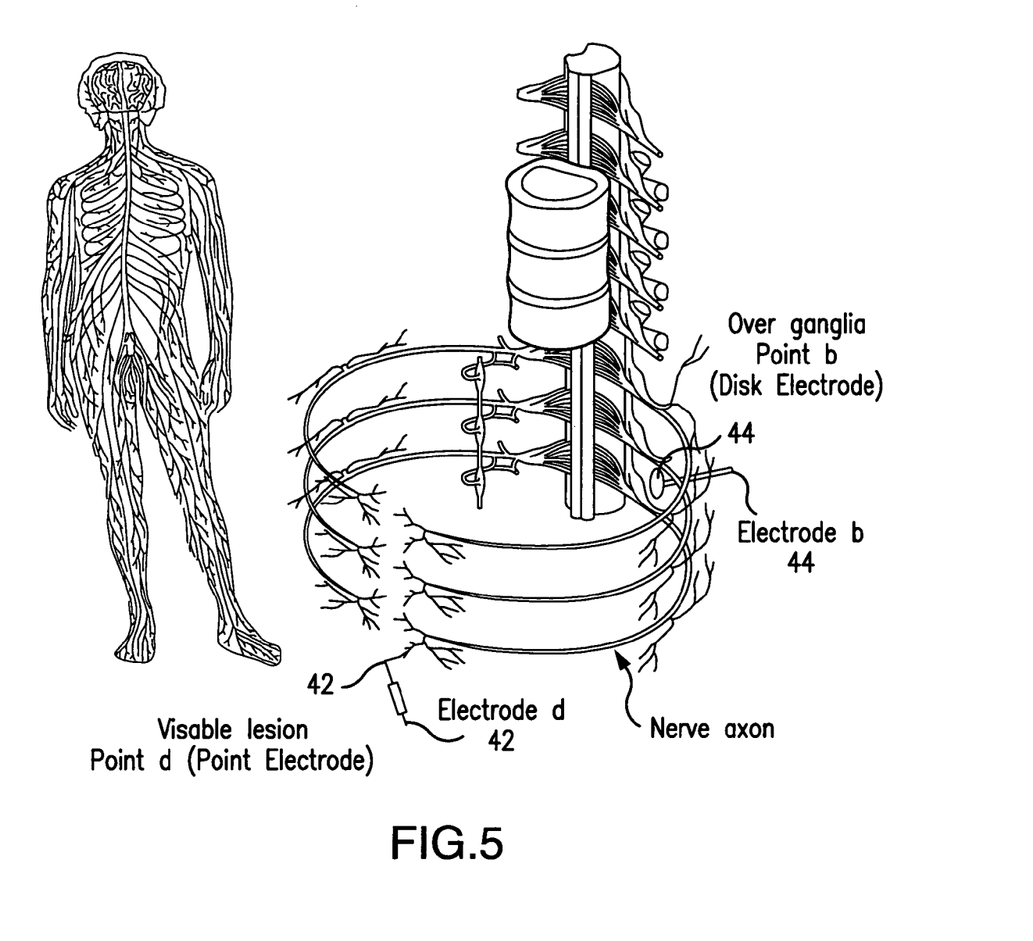
FIG. 5 depicts the targeting a nerve.

Referring to FIG. 5, the electrodes 42,44 are analogous to the electrodes 24,26 on either side of the capacitor 12 of FIG. 2, in the resonating RLC circuit. Each electrode is placed in close proximity to each end of the target nerve axon. An example would be placing one disk shaped electrode on the surface of the back over the appropriate ganglia and placing the other point shaped electrode on the lesion. This could target a neuron infected with the herpes virus.

The herpes example only demonstrates how a neuron or group of neurons can be targeted for any application. By studying the anatomy of the nervous system. It can be see that any sensory or motor nerve could be targeted. If one electrode is placed over its ganglia and the other electrode is place over the area of pain. The nerve could be incinerated or only numbed depending on the applied current. This means the nerve resonator could have numerous applications. For example in density it could replace conventional Novocain. Technicians in the field could use it to instantly numb an injured victim as well as surgeons could use it to perform surgery. It could be used in sports medicine to treat arthritis or other injuries. It could also be used to treat other viruses of the nervous system. It could also be used to replace conventional shock treatments making it less painful for the mental patient. The placement of the electrodes used for the nerve resonator is much like the placement of pins used in acupuncture. The system could also be used in place of conventional TENS and NMES devises. Its main difference is the nerve resonator is tuned in each application. This device could also be used to stimulate neural pathways in the brain. Regardless of the condition of the neurotransmitters they will have a unique capacitance and can be matched with the proper inductance for the given natural frequency.

Applying a voltage across the electrodes and measuring the capacitance can find the precise location of the electrode that is placed on the back. With one electrode on the lesion the other electrode can be moved around on the back, in close proximity to the location over the appropriate ganglia, until a maximum capacitance is measures for a given voltage. A dielectric may be needed on the skin to eliminate a conducting surface charge. The electrodes will have a maximum charge for a given voltage because the capacitance is a maximum and charge is directly proportional to capacitance.

$$C = \frac{Q}{V}$$

The following equation shows capacitance is directly proportional to the area and inversely proportional to the distance.

$$C = \frac{\varepsilon A}{d}$$

If electrode 42 has a very small area (A), and the distance (d) between the electrodes is relatively large, the capacitance would be extremely small. When the body is placed between the electrodes the capacitance increases and can be broken down into two components. One component is the 42 to nerve capacitance and the other component is the b 44 to nerve capacitance. These distances are much smaller than the free space distance between the electrodes with no body present. The total capacitance is composed of the individual capacitance components. The capacitance model in FIG. 5 shows this. The capacitance model also shows how the displacement current will affect the conductive nerve axon since it has a smaller resistance (R) than the surrounding tissue.

The conductive material in the nerve axon is known to be an electrolyte. The electrolyte is potassium ions. When an electrolyte is exposed to a current the result is electrolysis. If the current destroys the nerve with electrolysis or if the current destroys the nerve with heating the net result is the nerves conductivity is destroyed. This will change the capacitance ($C_{bd}$) and the system will no longer resonate with the same inductance (L) and natural frequency ($\omega_0$). This condition will indicate the nerve axon is incapacitated.

Figure 6:
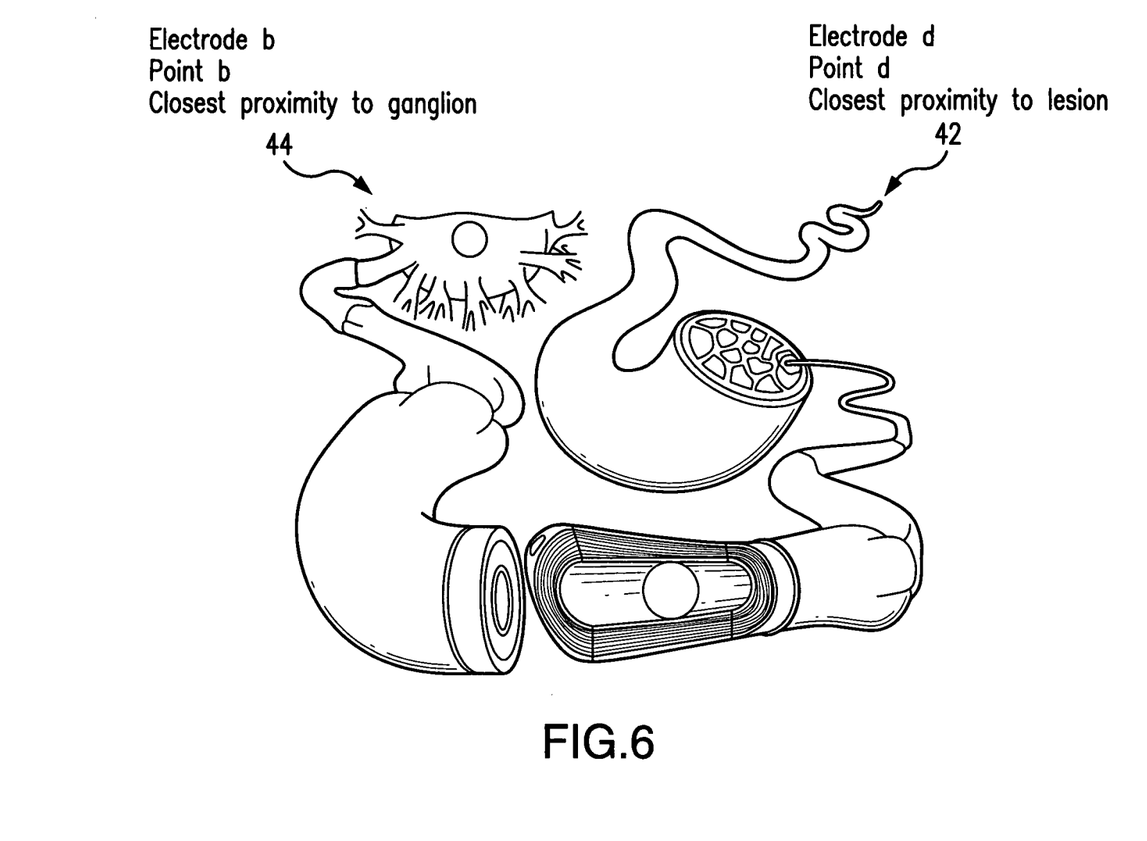
FIG. 6 depicts a second use of the invention on a nerve.

Although, a single nerve axon has a very small cross section, a nerve is made up of hundreds of axons as shown in FIG. 6. This should significantly increase the area of the conductive cross section through the tissue in the capacitance model shown in FIG. 3. Although the model is simplified it makes the point that there exists a unique capacitance ($C_{bd}$) between the electrodes 44 and 42. The capacitance ($C_{bd}$), connected in place of the capacitance (C), will become the new capacitance of the RLC circuit. The new capacitance ($C_{bd}$)) has a unique natural frequency ($\omega_0$) for a unique inductance (L).

Figure 7:
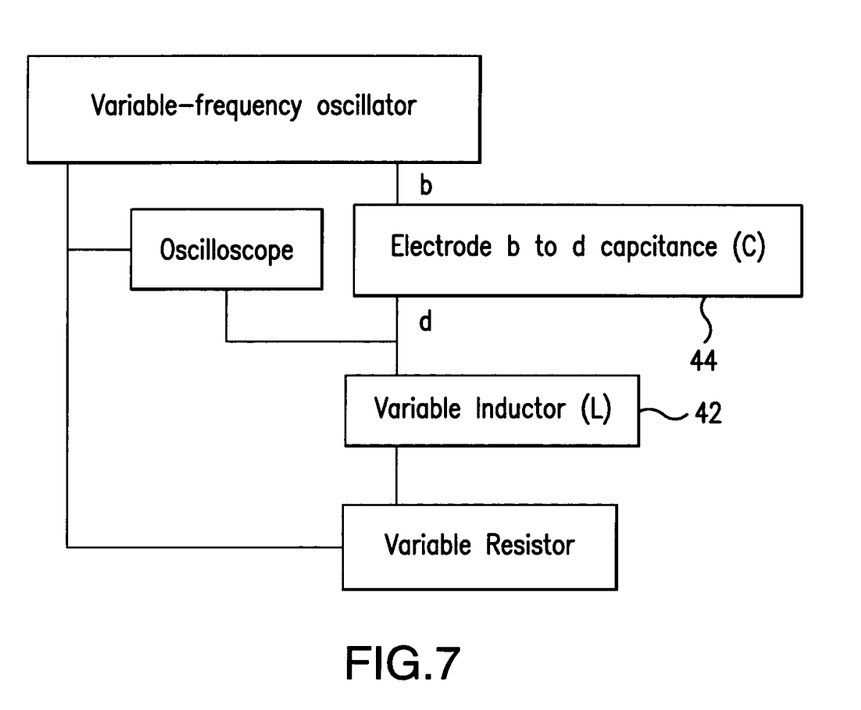
FIG. 7 schematically shows an instrument to treat a nerve.

As shown in the schematic in FIG. 7, the system consists of a variable frequency oscillator, a variable resistor, an oscilloscope, a variable inductor, and the capacitance between the two electrodes 44 and 42. The variable-frequency oscillator generates the alternating current. This frequency could be around $20^6$ Hz or more. Once the electrodes are placed on the body the capacitance between electrode 44 and 42 ($C_{bd}$) becomes the new capacitance (C). After the electrodes are placed on the body the capacitance between them can be measured. For the herpes example the maximum capacitance for a given voltage will indicate the optimum position of the electrode placed on the back over the ganglia. This capacitance will indicate a unique inductance (L) required for the system to resonate at a given natural frequency ($\omega_0$). The oscilloscope will indicate when the system is resonating. The circuit can be tuned by adjusting the inductance for a unique frequency. Once the system is resonating at the natural frequency the variable resistor can be used to adjust the current in the system At resonance the increasing displacement current induced in the axon will cause it to become an insulator. This will change the capacitance ($C_{bd}$) of the system. The change in capacitance will result in a change in the systems natural frequency and the system will no longer resonate. This change indicates the neuron has been disabled. The same result could be achieved by varying the frequency ($\omega$)for a given inductance (L).

The simplest way to view this system is to remember it is basically a simple resonating RLC circuit. Two electrodes are placed at designated positions relative to a target nerve axon. In a resonating RLC circuit the current obeys Ohm's law and can be set with voltage and resistance.

$$V_R = IR$$

In other words the nerve fiber becomes part of the circuit. For example if current required is in the range from 0.1 A to 1 A you would use a variable resistor with a range of $10\Omega$-$1\Omega$ and a voltage of 1V.

Figure 9:
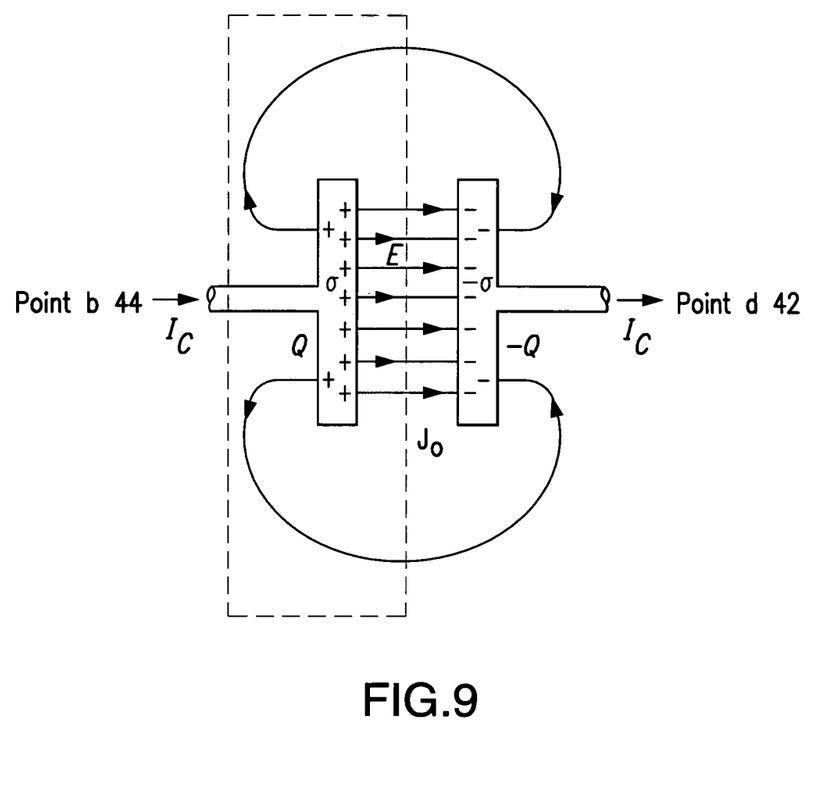
FIG. 9 depicts current through a capacitor.

The displacement current density ($J_D$) as seen in FIG. 9, between the plates of a capacitor, is related to the conduction current ($I_C$) in the circuit. The plates can be viewed as the electrodes as shown in the capacitance model seen in FIG. 3. As seen in the following equation the conduction current ($I_C$) going into one electrode equals the product of the displacement current density ($J_D$) and the area between the electrodes.

$$I_C = J_D A$$

The displacement currents will affect a conductor, in the dielectric, between two electrodes. The displacement current density ($J_D$) between the electrodes is directly proportional to the electric field rate of change $$\left(\frac{dE}{dt}\right)$$

between the electrodes. This relationship is illustrated in the following equation.

$$J_D = K\varepsilon_0 \left(\frac{dE}{dt}\right)$$

This equation indicates that since there is an electric field rate of change between the plates in a resonating RLC circuit there will be a displacement current affecting the area between the plates. Since electrode 44 and electrode 42 act like the two plates of a capacitor the nerve axon between the electrodes will see displacement currents. If a capacitor was made with a conductor in it and an increasing alternating current was applied to the capacitor it would eventually short across the conductor. This example illustrates how the displacement currents affect a conductor in changing electric field.

To test this device the RLC circuit system schematically shown in FIG. 7 could be used. A frequency of around $10^6$ Hz can be used on the nervous system. Therefore it could be used as a starting point. The electrodes 44 and 42 are placed in the closest proximity to the target nerve. Electrode 44 is an insulated and shielded disk and electrode 42 is an insulated and shielded point, as seen in FIG. 4. Electrode 44 is placed over the approximate area of the target ganglia. The ganglion is located along the spine. Electrode 42 is a disk to minimize the distance to the cell nucleus in the ganglia. Electrode 44 is a point because it is placed over the target area, on the skin, and is designed to target the nerve axon ending at that point. We could target more neurons by making electrode 44 a disk. This would depend on the application. Both electrodes are insulated on the ends but not shielded on the ends. The precise location of the 42 electrode, placed on the back over the ganglia, is found by applying a voltage across the electrodes with the electrode 44 placed on the targeted skin area. The capacitance can then be measured in real time. The location of the electrode 42 is where maximum capacitance is measured.

Figure 8:
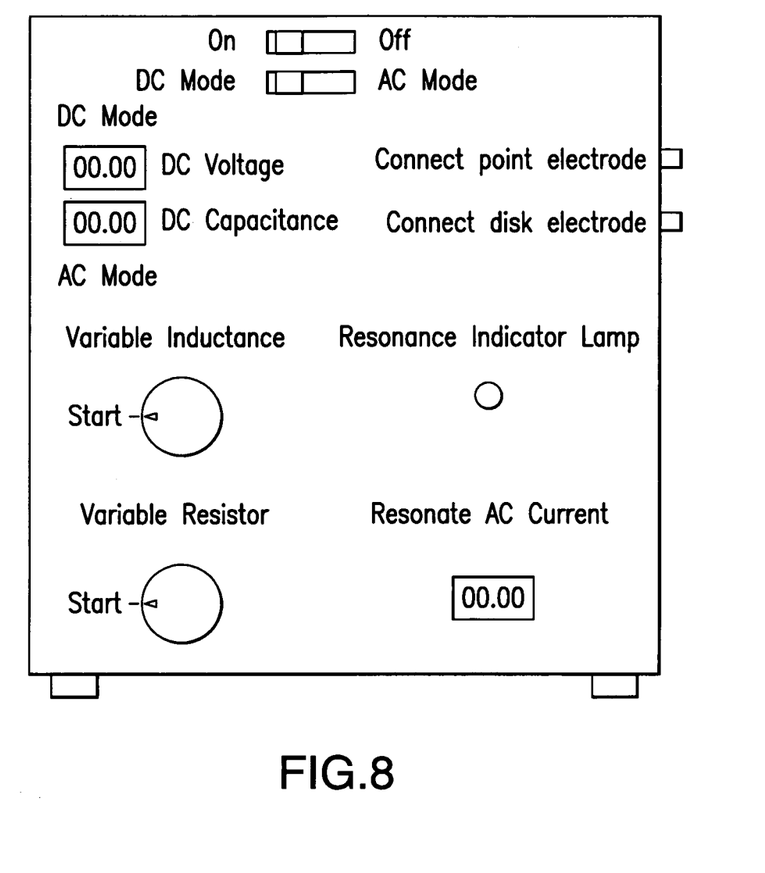
FIG. 8 depicts a system to treat a nerve.

This capacitance has a unique inductance for a set natural frequency. An oscilloscope can be used to indicate when resonance is achieved by adjusting the inductance for the set natural frequency. Once resonance is achieved, with the electrodes on the body, the variable resistor can control the displacement current. When the displacement current increases in the nerve axon it will heat up until it thermally breaks down and becomes an insulator. This can be illustrated by the example of a shorting capacitor. The oscilloscope will then indicate when the system is no longer resonating because the capacitance has been changed. This indicates that the nerve has been incapacitated. As seen in FIG. 8 the actual electronic device could be lightweight and portable. An operator could easily operate the device by following simple instructions:

The following shows the instructions for this device.
1: Turn device on
2: Switch to DC mode.
3: Place point electrode on lesion.
4: Place disk electrode on back over the ganglion.
5: Move the disk electrode around until the capacitance is at its maximum.
6: Make sure both adjustment knobs are in the start position.
7: Switch to AC mode.
8: Rotate the variable inductance knob until resonance lamp comes on.
9: Rotate the variable resistance knob until the resonance indicator lamp goes off.
10: When the resonance indicator lamp goes off the nerve has been incapacitated.

The alternating current can be analog or digital. An inductor and a capacitor can cause an electric circuit to resonate just as a spring and a mass can cause a mechanical system to resonate. Two electrodes places near each end of the target axon have their own unique capacitance. If this capacitance replaces the capacitor, in a resonating RLC circuit, the circuit has a new natural frequency and or inductance. In order for the new circuit to resonate it must be oscillated at its new natural frequency or the inductance must be adjusted to achieve the original natural frequency. Once the circuit is resonating the alternating field change between the electrodes can cause a displacement current between them. This current can be manipulated with a variable resister because, when an RLC circuit is resonating, the current obeys Ohm's law. The displacement currents affect any dielectric between the electrodes. This affect can be used to create a current in the conductive nerve axons within the dielectric tissue. This current can then be used to disable a targeted nerve.

The basic concept is that an alternating current can be induced on the axon of a neuron by use of an RLC circuit. The target can a single nerve axon or multiple nerve axons and will be affected by two electrodes creating the capacitance in the circuit. The circuit can then be tuned to resonate and a current induced on the target nerve axon. The alternating current can be used for heating or any other purpose. It is also noticed that a similar resonating system could be built with one electrode or multiple electrodes.

I claim:

1. A system comprising:
a variable inductor adapted to change a resonant frequency of a series RLC circuit;
a first electrode;
a second electrode, said variable inductor, said first electrode and said second electrode comprised by said series RLC circuit, said series RLC circuit electrically coupled to a plurality of targeted neurons, said series RLC circuit formed via placing said first electrode and said second electrode on opposing surfaces of said plurality of targeted neurons, wherein a discontinuity between said plurality of targeted neurons and said first electrode and said second electrode make up at least part of capacitive reactance of said series RLC circuit.

2. The system of claim 1, wherein:
said plurality of targeted neurons are electrically coupled to said first electrode and said second electrode and said plurality of targeted neurons act as electrical conductors, with inherent inductive and capacitive reactance, in said RLC circuit.

3. The system of claim 1, further comprising:
an oscilloscope adapted to provide information to a user to allow a user to tune said series RLC circuit to said resonant frequency.

4. The system of claim 1, further comprising:
a variable resistor adapted to be adjusted to change an electric current flowing through said series RLC circuit.

5. The system of claim 1, wherein:
a lamp electrically coupled to said series RLC circuit, said lamp adapted to come on when said series RLC circuit is operating at said resonant frequency, said lamp adapted to go off when a neuron of said plurality of targeted neurons has been incapacitated.

6. The system of claim 1, wherein:
said variable inductor is a secondary winding of a Tesla coil; and
electromagnetic energy is supplied to said RLC circuit via said Tesla coil.

7. The system of claim 1, wherein:
said variable inductor is a secondary winding of a modulated Tesla coil; and
electromagnetic energy is supplied to said RLC circuit via said Tesla coil.

8. A method comprising a plurality of activities, comprising:
causing electromagnetic stimulation in a plurality of targeted neurons via placement of a first electrode and a second electrode on opposing surfaces electrically coupled to said plurality of targeted neurons, said plurality of targeted neurons at least part of a total capacitance and inductance of a series RLC circuit, said series RLC circuit comprising said first electrode and said second electrode coupled in series with a variable inductor, said variable inductor adapted to change an inductive reactance of a series RLC circuit, said inductive reactance adjusted such that it is approximately equal in magnitude to a capacitive reactance of said series RLC circuit at a given resonant frequency.

9. The method of claim 8, further comprising:
targeting a neuron in said plurality of targeted neurons for electromagnetic stimulation via said series RLC circuit.

10. The method of claim 8, further comprising:
targeting a neuron in said plurality of targeted neurons for treatment via said series RLC circuit.

11. The method of claim 8, further comprising:
tuning said variable inductor to cause said series RLC circuit to operate at said given resonant frequency.

12. The method of claim 8, further comprising:
cauterizing a neuron of said plurality of targeted neurons via an alternating current in said series RLC circuit, wherein said neuron of said plurality of targeted neurons is in a targeted area between said first electrode and said second electrode.

13. The method of claim 8, further comprising:
via an electric current in said series RLC circuit, causing an electrolyte in a neuron to become a dielectric.

14. The method of claim 8, further comprising:
via placement of electrodes, targeting infected neurons comprised by said plurality of targeted neurons for treatment.

15. The method of claim 8, further comprising:
via placement of electrodes, thermally breaking down a neuron comprised by said plurality of targeted neurons.

16. The method of claim 8, further comprising:

via an electric current in said series RLC circuit, numbing a neuron comprised by said plurality of targeted neurons.

17. The method of claim 8, further comprising:

adjusting said variable inductor to change a natural resonating frequency of said series RLC circuit.

18. The method of claim 8, further comprising:

monitoring a change of a capacitive and inductive reactance in a neuron of said plurality of neurons in said series RLC circuit by monitoring a change in resonant frequency for a given inductive reactance in said RLC circuit.

19. The method of claim 8, further comprising:

monitoring a change of a capacitive and inductive reactance in a neuron of said plurality of neurons in said series RLC circuit by monitoring a change in inductive reactance for a given resonant frequency in said RLC circuit.

20. The method of claim 8, further comprising:

adjusting said variable inductor to tune in a resonating frequency of said series RLC circuit by monitoring a change in charge on each electrode.

21. The method of claim 8, further comprising:

using coils as electrodes or in conjunction with electrodes to change a magnetic component of electromagnetic energy transfer across a neuron of said polarity of neurons.

22. The method of claim 8, further comprising:

increasing or decreasing a voltage or current in said RLC circuit by increasing or decreasing a voltage or current of a power supply of said RLC circuit.

23. The method of claim 8, further comprising:

causing polarization, depolarization or neutralization of a neuron of said plurality of neurons in said RLC circuit.

24. The method of claim 8, further comprising:

tuning a frequency to said given resonant frequency of said series RLC circuit for a given non-variable or preset inductive reactance.

25. The method of claim 8, wherein:

said first electrode or said second electrode or both electrodes are electrically insulated.

26. The method of claim 8, wherein:

said first electrode or said second electrode or both electrodes are replaced with multiple electrodes.

* * * * *